(12) United States Patent
Meisner (10) Patent No.: US 7,834,055 B2
(45) Date of Patent: *Nov. 16, 2010

(54) COMPOSITIONS AND METHODS FOR THE TREATMENT OF SKIN

(75) Inventor: Lorraine Faxon Meisner, Madison, WI (US)

(73) Assignee: Bioderm, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/015,258

(22) Filed: Jan. 16, 2008

(65) Prior Publication Data

US 2008/0125395 A1    May 29, 2008

Related U.S. Application Data

(63) Continuation of application No. 09/997,663, filed on Nov. 29, 2001, which is a continuation-in-part of application No. 09/732,385, filed on Dec. 7, 2000, now Pat. No. 6,444,699, which is a continuation of application No. 09/356,142, filed on Jul. 19, 1999, now Pat. No. 6,217,914.

(60) Provisional application No. 60/125,356, filed on Mar. 19, 1999.

(51) Int. Cl.
A61K 31/375 (2006.01)
A61K 31/7008 (2006.01)
A61P 17/00 (2006.01)
A61P 17/10 (2006.01)

(52) U.S. Cl. ........................ 514/474; 514/62
(58) Field of Classification Search ................. None
See application file for complete search history.

(56) References Cited

U.S. PATENT DOCUMENTS

| | | | |
|---|---|---|---|
| 2,400,171 A | 5/1946 | Ruskin et al. |
| 2,442,461 A | 6/1948 | Karrer |
| 2,517,276 A | 8/1950 | Bassford et al. |
| 2,585,580 A | 2/1952 | Oppit |
| 3,857,939 A | 12/1974 | Green et al. |
| 3,857,970 A | 12/1974 | Tsumura et al. |
| 3,886,265 A | 5/1975 | Evers et al. |
| 4,229,430 A | 10/1980 | Fahim et al. |
| 4,294,852 A | 10/1981 | Wildnauer et al. |
| 4,367,157 A | 1/1983 | Sherman |
| 4,515,771 A | 5/1985 | Fine |
| 4,590,067 A | 5/1986 | Meisner |
| 4,647,453 A | 3/1987 | Meisner |
| 4,711,780 A | 12/1987 | Fahim |
| 4,722,936 A | 2/1988 | Jacob |
| 4,772,591 A | 9/1988 | Meisner |
| 4,818,521 A | 4/1989 | Tamabuchi |
| 4,894,978 A | 1/1990 | Schonmann et al. |
| 4,938,969 A | 7/1990 | Schinitsky et al. |
| 4,983,382 A | 1/1991 | Wilmott et al. |
| 5,140,043 A | 8/1992 | Darr et al. |
| 5,308,621 A | 5/1994 | Taylor et al. |
| 5,358,970 A | 10/1994 | Ruff et al. |
| 5,358,990 A | 10/1994 | Woodard et al. |
| 5,516,793 A | 5/1996 | Duffy |
| 5,554,647 A | 9/1996 | Perricone |
| 5,681,852 A | 10/1997 | Bissett |
| 5,700,451 A | 12/1997 | Yue et al. |
| 5,703,122 A | 12/1997 | Duffy |
| 5,736,567 A | 4/1998 | Cantin et al. |
| 5,750,123 A | 5/1998 | Znaiden et al. |
| 5,804,594 A | 9/1998 | Murad |
| 5,902,591 A | 5/1999 | Herstein |
| 5,972,993 A | 10/1999 | Ptchelintsev |
| 6,217,914 B1 | 4/2001 | Meisner |
| 6,440,465 B1 | 8/2002 | Meisner |
| 6,444,699 B2 | 9/2002 | Meisner |

(Continued)

FOREIGN PATENT DOCUMENTS

EP         281812 A1 *  9/1988

(Continued)

OTHER PUBLICATIONS

Remington's Pharmaceutical Sciences (17th Ed. 1985), p. 1293.*

(Continued)

*Primary Examiner*—Johann R Richter
*Assistant Examiner*—Frank I Choi
(74) *Attorney, Agent, or Firm*—Wilson Sonsini Goodrich & Rosati PC (57) ABSTRACT

An ascorbic acid-based composition and related method for the treatment of aging, photo-damaged or inflamed skin is disclosed. The composition includes water and ascorbic acid, at least a portion of which has generally been pretreated by being dissolved under relatively high temperature and concentration conditions. The composition typically includes at least about 5.0% (w/v) ascorbic acid formulated to have a pH above 3.5. 10 to 50% of the ascorbic acid is pretreated ascorbic acid. The composition may also include a non-toxic zinc salt, a tyrosine compound, and/or pharmaceutically acceptable carrier. The composition may include an anti-inflammatory compound, such as aminosugar and/or sulfur-containing anti-inflammatory compound. Embodiments containing an aminosugar such as glucosamine are further useful for treating rosacea and other inflammatory skin ailments. The composition may be administered in a variety of forms suitable for topical application on skin.

4 Claims, 3 Drawing Sheets

U.S. PATENT DOCUMENTS

| | | | |
|---|---|---|---|
| 2001/0041193 | A1 | 11/2001 | Meisner |
| 2002/0031557 | A1 | 3/2002 | Meisner |
| 2002/0164386 | A1 | 11/2002 | Meisner |
| 2005/0003023 | A1 | 1/2005 | Meisner |
| 2006/0165819 | A1 | 7/2006 | Meisner |

FOREIGN PATENT DOCUMENTS

| | | |
|---|---|---|
| EP | 0273202 B1 | 6/1995 |
| EP | 0771557 B1 | 8/1999 |
| JP | 61078715 | 4/1986 |
| WO | WO 98/23152 A1 | 6/1998 |
| WO | WO 00/56327 A1 | 9/2000 |
| WO | WO 01/83031 A2 | 11/2001 |
| WO | WO 01/83031 A3 | 4/2002 |

OTHER PUBLICATIONS

English Language Translation of EP 0771557 (2010).*

Setnikar, "Antireactive properties of glucosamine sulfate," Arzneimittel Forschung Drug Research 41:157-161, 1991.

Office Action mailed Mar. 17, 2008 in connection with U.S. Appl. No. 09/990,611, assigned to Bioderm, Inc.

Claims pending on Mar. 17, 2008 in connection with U.S. Appl. No. 09/990,611, assigned to Bioderm, Inc.

Office Action mailed Feb. 29, 2008 in connection with U.S. Appl. No. 09/997,663, assigned to Bioderm, Inc.

Claims pending on Feb. 29, 2008 in connection with U.S. Appl. No. 09/997,663, assigned to Bioderm, Inc.

Office Action mailed Jun. 13, 2006 in connection with U.S. Appl. No. 10/614,768, assigned to Bioderm, Inc., now abandoned.

Claims pending on Jun. 13, 2006 in connection with U.S. Appl. No. 10/614,768, assigned to Bioderm, Inc., now abandoned.

Office Action mailed Nov. 5, 2007 in connection with U.S. Appl. No. 11/389,384, assigned to Bioderm, Inc., now abandoned.

Claims pending on Nov. 5, 2007 in connection with U.S. Appl. No. 11/389,384, assigned to Bioderm, Inc., now abandoned.

Office Action mailed Nov. 2, 2007 in connection with U.S. Appl. No. 10/185,388, assigned to Bioderm, Inc.

Claims pending on Nov. 2, 2007 in connection with U.S. Appl. No. 10/185,388, assigned to Bioderm, Inc.

Ash, et al. Comparison of topical therapy for stiae alba (20% glycolic acid/0.05% tretinoin versus 20% glycolic acid/10% l-ascorbic acid). 1998, Dermatol Sur g 24:849-856.

Austria, et al. Stability of vitamin C derivatives in solution and topical formulations. 1997, J Pharm. Biomed. Anal. 15:795-801.

Bandelin, et al, "The Stability of Ascorbic Acid in Various Liquid Media", J. Am. Pharmacol. Assoc., 44(4), p. 241-244 (1955).

Bauerfeind. "Ascorbic Acid: Chemistry, Metabolism, Uses", Seib, et al., Advances in Chemistry, pp. 417-429 (1982).

Bekesi, et al., "Inhibitory Effect of D-Glucosamine and Other Sugar Analogs on the Viability and Transplantability of Ascites Tumor Cells", Cancer Research, 29, 353-359 (1969).

Black, H. S. "Potential Involvement of Free Radical Reactions in Ultraviolet Light-Mediated Cutaneous Damage", Photochemistry and Photobiology, 46: 213-221 (1987).

Borne, et al., "Antiinflammatory Activity of Para-Substituted N-Benzenesulfonyl Derivatives of Amino Acids", et al., J. Med. Chem., 15(12), 1325-1326 (1972).

Cooke, et al., "Vitamin C (Ascorbic Acid)", from conference in Warwick, Coventry (Apr. 1981), pp. 167-168, 170-171, Published by Applied Science Publishers.

Edward Staunton West, Ph.D., Wilbert R. Todd, Ph.D., Howard S. Nason, Ph.D. and John T. Van Bruggen, Ph.D. "Textbook of biochemi." Fourth Edition. 1966, pp. 823-795.

England, et al., "The Biochemical Functions of Ascorbic Acid", Ann. Rev. Nutri., 6:365-406 (1986).

Gualano, et al., "Anti-inflammatory Activity of S-Adenosyl-L-Methionie: Interface with the Eicosanoid System", Pharmacology Res. Commun., 15(7), 683-695 (Jul. 1983).

Hajratwala, B. R. "Stability of ascorbic acid", B. R. Stability of ascorbic acid. S.T.P. Pharma, 1(4), 281-286 (1985).

Hall, et al., "Anti-Inflammatory Activity of Diazomethyl Ketone and Chloromethyl Ketone Analogs Prepared from N-Tosyl Amino Acids", J. Pharm., 69(12), 1451-1452 (1989).

Hornig, et al., "Vitamin C (Ascorbic Acid)", from conference in Warwick, Coventry (Apr. 1981), pp. 225-226, Published by Applied Science Publishers.

Imai, et al., "The Antiscorbutic Activity of L-Ascorbic Acid Phosphate Given Orally and Percutaneously in Guinea Pigs", Jap. J. Pharmacol. Assoc., 317-324 (1967).

Jain, et al., "Evaluation of anti-inflammatory and analgesic properties of L-glutamine", Agents and Actions, 11(3), 243-248 (1981).

Kahn, et al., "Ultraviolet Light Protection by Several New Compounds", Arch Dermatol., 109, 510-517 (1974).

Kaplan, et al., "A New Stabilized Ascorbic Acid Solution: Percutaneous Absorption and Effect on Relative Collagen Synthsies", J. Cutaneous Aging & Cosmetic Derm., 1(2), 115-121 (1988/89).

Kassem, et al., "Studies on the stability of injectable L-ascorbic acid solutions: III. Effect of metal-complexing agents", Pharma. Acta Helvetiae, 47U, 89-97 (1972).

Kassem, et al., "Studies on the stability of injectable L-ascorbic acid solutions: I. Effect of pH , solvent, light and container", Pharmaceutica Acta Helvetiae, 44, 611-623 (1969).

Kolata, G. "Is Tyrosine the Key to Growth Control?" Science, 219, 377-378 (1983).

Kunert, et al., "The Effect of Vitamin C on in vivo Lipid Peroxidation in Guinea Pigs as measured by Pentane and Ethane Production", Lipids, 18, 271-273 (1983).

Kwapiszewski, et al., "Synthesis of L-Cysteine and S-Methyl-L-Cysteine Derivatives of Immunotropic and Anti-inflammatory Activity", Arch. Immunol. Et Ther. Exp., 27(6), 729-731 (1979).

Laszlo, et al., "Effects of Glucose Analogues (2-Deoxy-D-glucose, 2-Deoxy-D-galactose) on Experimental Tumors", Journal of the National Cancer Institute, 24, 267-278 (1960).

Lien, et al., "Topical Use of Ascorbic Acid in the Management of Pressure Sore", Formosan Med. Assoc., 75:243-250, (1976).

Litwin, J. "Growth of Human Diploid Fibroblasts in Media with Different Amino Acid Composition", J. Cell Science, 14, 671-678 (1974).

Nobile, et al., "Vitamin C", p. 23-24, MIP Press Ltd., Boston, MA (1981).

Paul A. Seib and Bert M. Tolbert. "Ascorbic acid: chemistry, metabolism and uses." American Chemical Society. 1992, pp. 419-423.

Pinnell, et al., "Cutaneous Aging," Eds. Kligman et al., Univ. of Tolyo Press, 275-292 (1988).

Smart, et al., "Inhibition of 12-O-Tetradecanoylphorbol-13-acetate Induction of Ornithine Decarboxylase Activity, DNA Synthesis, and Tumor Promotion in Mouse Skin by Ascorbic Acid and Ascorbyl Palmitate", Cancer Res., 47, 6633-6638 (1987).

STN Online, file CAPLUS, Acc. No. 1982:122495, Doc. No. 96:122495 (Kalus et al., Is there an equilibrium between ascorbic and dehydroascorbic acids?, Zeitschrift fuer Naturforschung, C:Journal of Biosciences (1981), vol. 36C, No. 11-12, pp. 1088-1090, Abstract.

Tapadinhas, et al., "Oral glucosamine sulphate in the management of arthrosis: report on a multi-centre open investigation in Portugal", Pharmatherapeutica, 3(3), 157-168 (1982).

The Merck Index: An Encyclopedia of Chemicals and Drugs. Windholz, et al. Eds. Merck and Co. 9th edition. Rahway, NJ. 1976; pp. 110-111 (#845-858).

Thomas, et al., "Anti-inflammatory activity of esters of phenylglycine", J. Pharm. Pharmacol., 26y(s), 151-152 (1974).

West, et al., "Textbook of Biochemistry", pp. 795, The MacMillan Company, New York (1951).

Yuan and Chen, "Degradation of Ascorbic Acid in Aqueous Solution," J. Agric. Food Chem. 46:5078-5082 (1998).

Miyake et al., "Formation mechanism of monodehydro-L-ascorbic acid and superoxide anion in the autoxidation of L-ascorbic acid," Biosci. Biotech. Biochem. 61(10):1693-1695 (1997).

Office action from corresponding Brazilian application No. PI 0009158-8 dated Jul. 30, 2009.

* cited by examiner

COMPOSITIONS AND METHODS FOR THE TREATMENT OF SKIN

This application is a continuation of application Ser. No. 09/997,663, filed on Nov. 29, 2001, which is a continuation-in-part of application Ser. No. 09/732,385, filed on Dec. 7, 2000, now U.S. Pat. No. 6,444,699, which is a continuation of application Ser. No. 09/356,142, filed Jul. 19, 1999, now U.S. Pat. No. 6,217,914, which claims the benefit of Provisional Application Ser. No. 60/125,356, filed on Mar. 19, 1999, the disclosure of each of which is incorporated by reference herein in its entirety.

BACKGROUND OF THE ART

Skin is composed of a top layer, the epidermis, which is approximately 20 cell layers or about 0.1 mm in thickness, and a lower layer, the dermis, which is from about 1 to about 4 mm in thickness and contains small blood vessels, collagen, elastin and fibroblasts. The dermis provides structural support and nutrients to the epidermis. Aging has been shown to increase cellular heterogeneity of the epidermal layer, however, it has little effect on the thickness of the epidermal layer. The supporting dermis, on the other hand, is known to thin with age and exposure to the sun and environmental contaminants. The dermal layer provides the support and blood supply for the epidermis, therefore the dermal layer is important in maintaining the elasticity and appearance of the skin. Disruption of the supporting dermis leads directly to sagging and consequent furrowing of the epidermis, i.e., the formation of wrinkles.

Deep wrinkles are also due to continual stretching and contraction of both the dermis and epidermis. Currently, these deep wrinkles or furrows may only be eliminated by plastic surgery or by collagen injections directly beneath the depressed areas. The fine wrinkles that occur with age and prolonged exposure to the sun and other environmental contaminants are the direct result of deterioration of the supporting dermal layer. Other environmental effects on the skin are discussed in U.S. Pat. Nos. 4,938,969 and 5,140,043.

As a result of the aging process and damage caused by incident radiation, a disruption of the collagen bundles that provide support to the epidermis is observed. Collagen exists normally in dense, organized patterns. During the aging process collagen becomes disorganized and less supportive of the epidermis and the dermis loses elasticity. There is also progressive loss of circulatory support from the small blood vessels that are more numerous and close to the surface in young skin. The result of aging on skin, whether or not it has been accelerated by incident radiation, is a deterioration of the dermal layer—fewer fibroblasts, less collagen, less elastin and less circulatory support. Consequently, the normal stretching and contraction of the skin leads to damage of the dermis that is not readily corrected and wrinkling results.

Dermatologists and cosmetologists have directed their efforts to improving the appearance of skin using agents known to stimulate the growth and proliferation of epidermal cells. Newly proliferated cells provide more structure and hold more moisture, giving the skin a younger appearance. One method of causing new skin cell proliferation is accomplished by use of an irritant or chemical peel in which the uppermost layers of the epidermis are caused to slough off, leading to proliferation and replacement with new epidermal cells. While such treatment is recognized to provide some cosmetic improvement, it does not address the major causative factor, namely, the compromised supporting dermal layer.

Considerable effort has also been expended to find ways to prevent adverse changes in the skin brought about by ultra-violet (UV) exposure. Preventative approaches include physically blocking or absorbing the UV radiation before it can enter the skin using UV absorbing compounds. Blocking and absorbing are effective but are cumbersome because sun blockers or absorbers must be applied before every exposure and may be washed off with water. For example, after swimming UV absorbing compounds must typically be reapplied. Further, the long-term side effects of many of the compositions containing sun blockers and/or absorbers are not known.

L-ascorbic acid has many known biological functions from enzymatic cofactor to "sparing" agent against vitamin E depletion. See, for example, England and Seifter, "The Biochemical Functions of Ascorbic Acid," Ann. Rev. Nutri. 6:365-406, (1986); Kunert and Tappel, "The Effect of Vitamin C on in vivo Lipid Peroxidation in Guinea Pigs as Measured by Pentane and Ethane Production, Lipids 18:271-74 (1983). The latter function of L-ascorbic acid may partly account for its "anti-oxidant" status. Additionally, at higher concentrations, ascorbic acid is known to react with both the super oxide and hydroxyl radicals. The super oxide, and the hydrogen peroxide and hydroxyl radical subsequently generated, are oxygen-containing free radicals now known to be generated in vivo under a variety of normal and pathological conditions. These radicals have been implicated as causative agents for everything from sunburn to aging and are believed to destroy lipid membranes, break down DNA and inactivate enzymes, among other effects. An immense amount of work has been done in the last two decades documenting the deleterious behavior of oxygen radicals. Several recent texts on the subject include: Oxy-radicals in Molecular Biology & Pathology, D Cerutti, I. Fridovich, J. McCord, eds., (Alan R. Liss, Inc. New York, 1988); Biological Role of Reactive Oxygen Species in Skin, O. Hayaishi, S. Inamura, Y. Mayachi, eds. (Elsevier Press, New York, 1987); Free Radicals, Aging and Degenerative Diseases, J. E. Johnson, Jr., R. Walford, D. Harmon, J. Miguel, eds. (Alan Liss, Inc., New York, 1986); Free Radicals in Biology and Medicine, B. Halliwell and J. M. C. Gutteridge, eds., (Clarendon Press, Oxford, 1985); and Oxidative Stress Helmut Sies, ed. (Academic Press, 1985). Also addressing the subject are several symposia, including "Oxygen Radicals and Tissue Injury" Proceedings from an Upjohn Symposium (April, 1987); and "Oxygen Free Radicals," Proceedings from National Heart, Lung & Blood Institute (National Institute of Health, Washington, D.C., December 1987).

As a result of the known effects of the use of ascorbic acid on damaged and aging skin, there are now various Vitamin C or ascorbic acid ointments, serums and creams that are used with varying degrees of success to prevent and/or repair damage to the skin's dermal layer. For example, it has been reported that a composition including ascorbic acid, tyrosine and a non-toxic zinc salt, preferably zinc sulfate, in a vehicle suitable for topical application, when applied to areas showing the fine wrinkles associated with aging/sun exposure, results in a readily perceivable diminution of the fine wrinkle structure. It has also been reported that ascorbic acid topical aqueous compositions are unstable unless maintained at a pH below about 3.5. Topical compositions containing a carrier and a concentration of L-ascorbic acid above about 1% (w/v) may be stable if maintained at a pH below about 3.5 or even below about 2.5.

In addition to ameliorating skin damaged by age or environmental insult, topical ascorbic acid formulations may also exhibit some effectiveness in the treatment of various inflammatory skin maladies such as, for example, inflammatory rosacea, allergic inflammations and hypersensitivity. A few cases in which a topical formulation of ascorbic acid, zinc and tyrosine was applied to rosacea, for example, a slight improvement was observed with long-term use. Such formulations, however, have not been shown to clear up rosacea to a substantial extent and even slight improvement requires long-term, diligent daily application to the affected skin. Improved formulations of topical ascorbic acid are needed to effectively and quickly treat skin maladies such rosacea, allergic inflammations and hypersensitivity.

Currently available ascorbic acid compositions and methods fail to provide the delivery system for formulations having the desired combination of efficacy, non-irritability, stability and convenient storage solutions for topical Vitamin C applications. A significant problem of current compositions is that it is not practical to use more than 15% (w/v) ascorbic acid in a serum, cream gel or other suitable topical formulation for cosmetic use because the low inherent pH (circa 2-2.5) of such a formulation is often quite irritating to the skin. The breakdown of the ascorbic acid in such low pH formulations due to exposure to water, heat, and air can also lead to undesirable discoloration and eventually loss of efficacy. Furthermore, if the ascorbic acid is formulated in a cream with limited water content to enhance stability of the ascorbic acid over time, changes in heat, atmospheric pressure and/or moisture content may activate the ascorbic acid, leading to unacceptable expansion and even explosion of the containers holding such creams or gels. There is, therefore, a continuing need for topical ascorbic acid-based compositions that improve the efficacy and stability of such skin treatment formulations.

SUMMARY OF THE INVENTION

The present invention provides stable, effective topical compositions that include ascorbic acid, generally in a relatively high pH formulation. The concentration of active ascorbic acid that is available to be delivered to the skin is maintained at a high concentration, while at the same time lowering the irritating effects commonly associated with aqueous compositions having a high concentration of organic acid. By providing, for example, a portion of the total ascorbic acid of the composition in the ascorbate salt form, the composition disclosed herein decreases the overall irritant nature of the solution without losing efficacy or desired biological effect. The present ascorbic acid-based composition are particularly effective for topical application to reduce epidermal wrinkling, such as that resulting from intrinsic aging or photo damage. For example, applying the present compositions within about six hours to skin that has received excess sun damage can attenuate the effects due to UV exposure and decrease sunburn and cell damage. In addition, the compositions disclosed herein did not expand or lose integrity on storage. The present compositions were also far less likely to oxidize to yield an off color (e.g., to become darker or brown). Subjects using the present ascorbic acid formulations found the product to be very effective, and to yield rapid results relative to decreasing the appearance of fine lines.

In addition to treating aged or damaged skin, the present invention further includes compositions and methods for treating inflammatory skin ailments such as inflammatory rosacea. The present invention provides formulations of ascorbic acid in combination with an anti-inflammatory agent such as, for example, glucosamine or other suitable aminosugar. Such combination formulations demonstrate significant improvement in the treatment of inflammatory ailments of the skin such as, for example, rosacea, in comparison to formulations of ascorbic acid without, for example, glucosamine. Formulations of the present invention that include glucosamine are particularly useful over prior art formulations for treating inflammatory ailments of the skin that have demonstrated resistance to prior art treatments.

Conventional treatment for rosacea is cortisone therapy. Long-term use of cortisone is undesirable, however, because it weakens the strength and resilience of connective tissue. Another drawback of cortisone use is the rebound effect that occurs when the use of cortisone is temporarily discontinued. The present invention provides a treatment for rosacea that does not have the undesirable effects of cortisone and that is effective for individuals that are resistant to cortisone treatment. Methods are provided to combine glucosamine, for example, with ascorbic acid so that the ingredients maintain efficacy and achieve a stable shelf life in formulations suitable for topical application to the skin.

The present compositions typically include up to about 50% of the total ascorbic acid present that has been prepared by dissolution in water at relatively high temperature and concentration. Ascorbic acid dissolved in this manner is referred to herein as "pretreated" ascorbic acid and is prepared by dissolving a high concentration of ascorbic acid, typically at least about 20% (w/v) (i.e., at least about 200 mg/ml) in water at 60° to 90° C.

Importantly, compositions of a cream, or other suitable administration form of the present invention, containing 50% (w/v) ascorbic acid content in the form of pretreated ascorbic acid, formulated as described herein, are stable. That is, such compositions do not expand, explode, or discolor due to heat, changes in atmospheric pressure, or improper storage, all of which have proved to be problems in manufacturing, storing and distributing formulations of pure L-ascorbic acid and its direct break down products. Further, compositions of the present invention that comprise a combination of pretreated ascorbic acid and glucosamine are also stable.

Embodiments of the present compositions commonly include water, at least about 5.0% (w/v) ascorbic acid, and have a pH of more than 3.5. The compositions typically also include (a) non-toxic zinc salt and/or (b) a stimulant of protein synthesis and/or precursor to melanin synthesis (e.g., a tyrosine compound). The compositions may also include an anti-inflammatory compound, such as an aminosugar and/or a sulfur-containing anti-inflammatory compound. The topical compositions may be in any of a number of common forms, such as an aqueous solution ("a serum"), a hydrophilic lotion-, an ointment-, a cream or a gel. Typically, the topical composition includes a pharmaceutically acceptable carrier and may also include one or more other formulation additives, such as surfactant(s), thickener(s), dyes, other antioxidants and/or fragrance.

The "high pH" formulations of the present compositions are less irritating than high concentrations of L-ascorbic acid (with its inherent low pH, e.g., circa 2.0-2.5) because the relatively higher pH avoids the skin irritation problem often encountered with harsh chemical peels or solutions with pH values below 3.5. The present compositions were also found to be very stable on short and long term storage, while maintaining a high degree of effectiveness.

The present invention also includes a method of treating damage to skin, such as often arises due ultraviolet light exposure and/or aging, as well as treating rosacea or other inflammatory skin afflictions. The method includes applying the present topical composition to a damaged or afflicted portion of the skin. For example, the present composition is typically applied topically to the locus of wrinkles or the locus of rosacea.

BRIEF DESCRIPTION OF THE FIGURES

The invention will become more fully understood from the following detailed description, taken in conjunction with the accompanying drawings, in which.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

Long shelf-life and extended stability (e.g., for at least two years) is normally required for any cosmetic product to be distributed through ordinary channels in which there must be stored inventory to meet market demand without the concern that the inventory will deteriorate before being sold. The present ascorbic acid-based compositions have good efficacy and storage stability, and low skin irritability. These topical ascorbic acid based compositions are particularly effective for reducing epidermal wrinkling resulting from intrinsic aging or photo damage. The compositions of the present invention may also be used prophylactically to ameliorate the photo-induced damage that results from exposure of skin to sunlight and other harmful irradiation. Additionally, embodiments of the present invention in which ascorbic acid and glucosamine are combined are useful for treating skin afflicted with rosacea or other inflammatory skin conditions.

The compositions typically include at least about 5.0% (w/v) ascorbic acid. Herein, the amount of ascorbic acid present in a composition refers to the total amount of ascorbic acid and ascorbate present stated as if all was present in the acid form. In other words, a solution which includes 0.5 mole ascorbic acid and 0.5 mole of an ascorbate salt contains the same total amount of ascorbic acid as a solutions which include either 1.0 mole ascorbic acid or 1.0 mole of an ascorbate salt.

The present compositions commonly include at least about 5.0% (w/v) total ascorbic acid, which may comprise ascorbic acid in the form of monohydroascorbic acid or ascorbate salts. It is generally advantageous to include higher concentrations of ascorbic acid, typically at least about 10% (w/v) and often concentrations in the range of about 15 to about 25% (w/v) ascorbic acid. Because of the potential problems of skin irritation with formulations containing high concentrations of ascorbic acid, it is generally advantageous to adjust the pH of such formulations to at least about 3.5. To achieve an optimum combination of low irritability and high stability, the present compositions are typically formulated to have a pH of about 3.7 to about 4.1 and, for example, between about 3.8 to about 4.0. Compositions of the present invention may further include anti-inflammatory agents such as glucosamine in combination with ascorbic acid.

It has been found that ascorbic acid-based topical formulations in which a substantial portion of the ascorbic acid has been pretreated in accordance with the present invention exhibit particularly good storage stability. As noted above, for the purposes of this application, "pretreated" ascorbic acid also refers to ascorbic acid that has been dissolved in water at a relatively high temperature to form a concentrated ascorbic acid solution. Typically, the ascorbic acid is dissolved in water at between about 60 to about 90° C. (e.g., between about 75 to about 80° C.) to form a concentrated solution that contains at least about 20% (w/v) ascorbic acid. The ascorbic acid is dissolved in the acid form, i.e., the resulting solution will have a relatively low pH (circa 2.0-2.5). After dissolution, the concentrate is generally heated for an additional period of time (e.g., 0.25 to 1.0 hour) and cooled to below about 40° C. before being incorporated into the final formulation. If the pretreated ascorbic acid concentrate is to be stored prior to formulation, it may be stored at room temperature or below (e.g., about 3 to about 20° C.) and/or under conditions that exclude oxygen-containing gases such as air (e.g., in a sealed container or blanketed with an inert gas such as argon or nitrogen). In the present compositions, at least about 10% of the ascorbic acid present may be pretreated ascorbic acid. Typically, no more than about 50% of the ascorbic acid present has been pretreated to obtain the enhanced stability properties of the compositions while minimizing the additional processing steps and costs associated with the pretreatment of the ascorbic acid.

Figure 1:
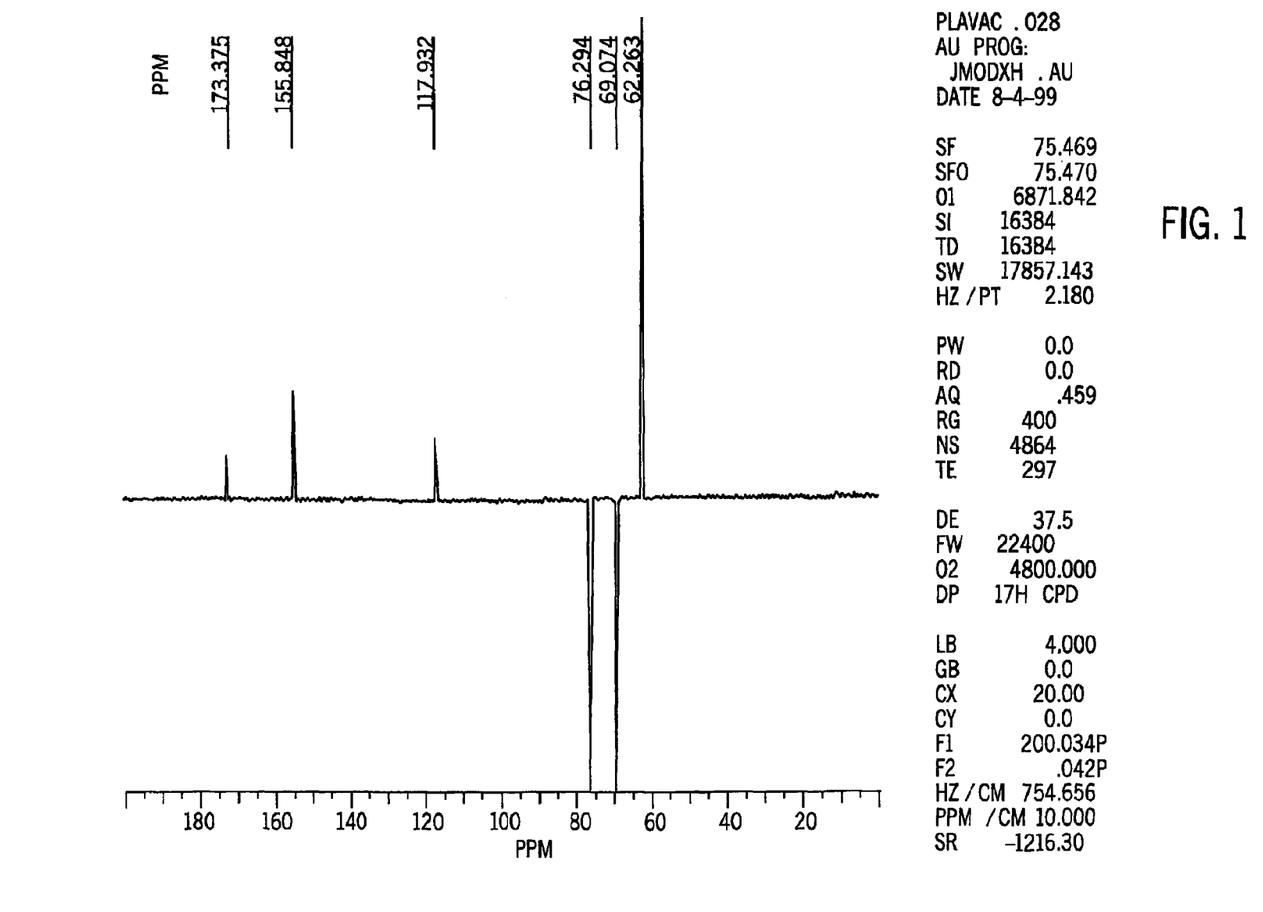
FIG. 1 shows a $C^{13}$ NMR of a 10% (w/v) solution of "native" ascorbic acid after storage for one week at 37° C.
Figure 2:
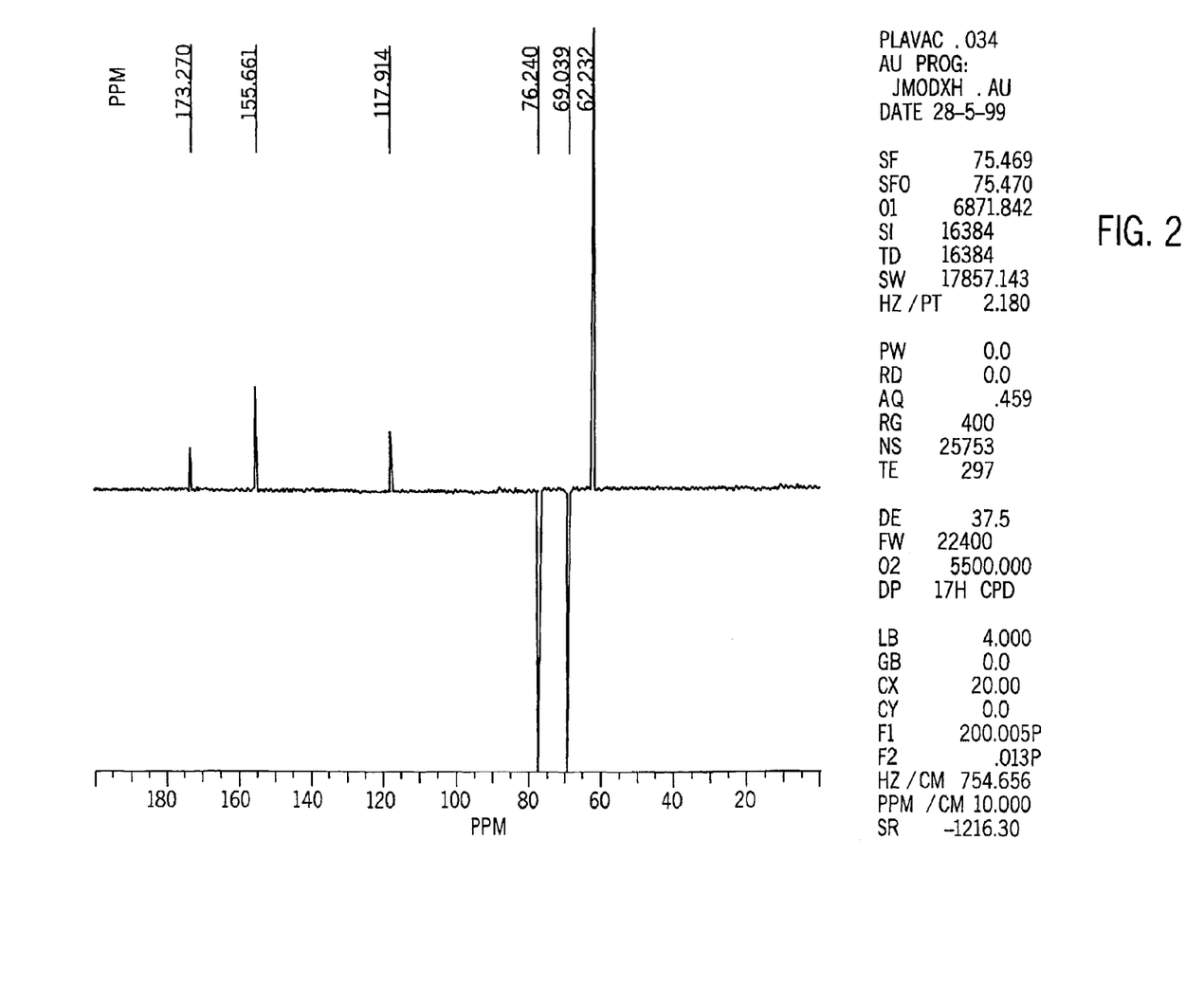
FIG. 2 shows a $C^{13}$ NMR of a 1:1 mixture of a 10% (w/v) solution of "native" ascorbic acid and a 30% (w/v) solution of pretreated ascorbic acid after storage of the mixture (at pH 2.3) for one month at room temperature.
Figure 3:
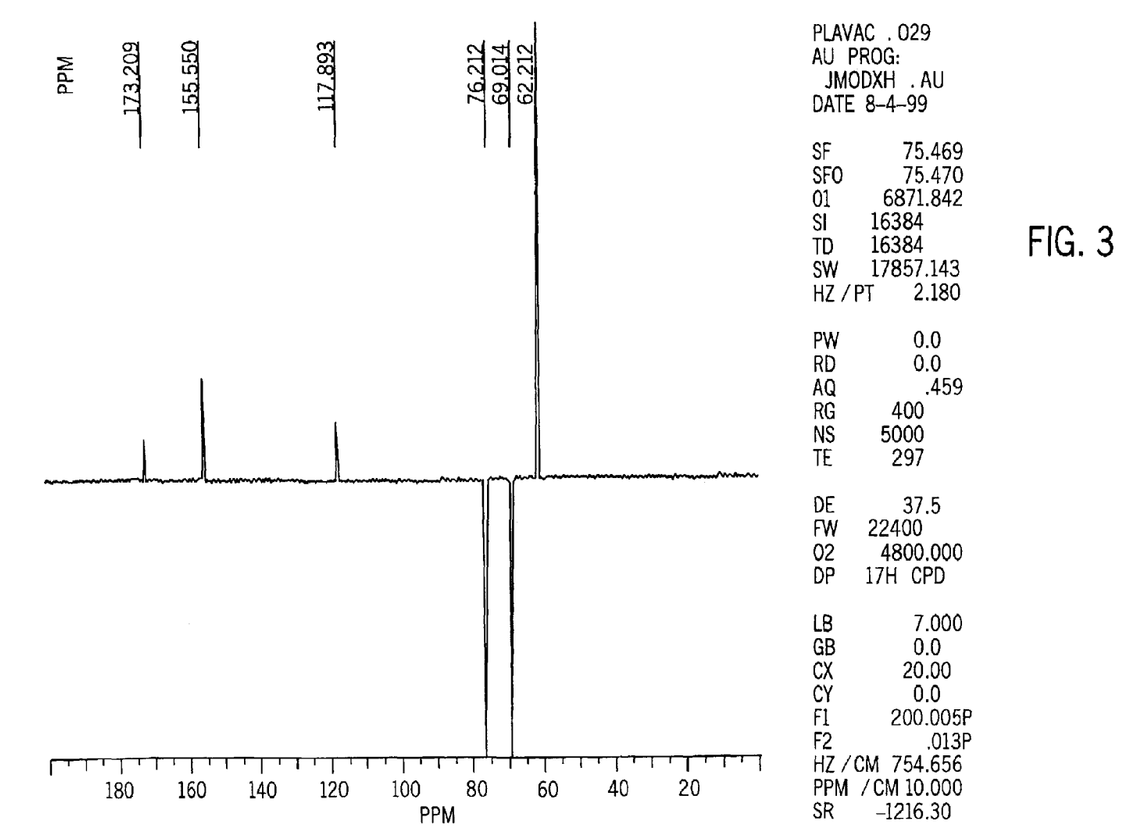
FIG. 3 shows a $C^{13}$ NMR of a 30% (w/v) solution of pretreated ascorbic acid after storage for one week at 37° C.

To test and quantitate the stability of composition containing pretreated ascorbic acid, nuclear magnetic resonance (NMR) spectra of stored samples of the following ascorbic acid-based solutions: (i) a 10% (w/v) solution of "native" ascorbic acid; (ii) a 1:1 mixture of the 10% (w/v) solution of "native" ascorbic acid and a 30% (w/v) solution of pretreated ascorbic acid; and (ii) the 30% (w/v) solution of pretreated ascorbic acid after storage. The results, shown in FIGS. 1, 2 and 3 respectively, demonstrate the stability of the solutions under storage conditions. Somewhat accelerated storage testing is often carried out by storing solutions at 37° C. The results of tests (see, e.g., FIGS. 1 and 3) demonstrated that both a 10% (w/v) solution of "native" ascorbic acid and a 30% (w/v) solution of pretreated ascorbic acid were stable after storage at 37° C. for one week.

As an example, containers having a 1 to 20% (w/v) concentration of a mixture of pretreated ascorbic acid in a 1:1 to 1:10 ratio, together with ascorbic acid formulated under more standard conditions (i.e., dissolved or added in solid form to a formulation at temperatures of about 20 to about 40° C.—"native ascorbic acid") were quite stable when shipped and/or stored under adverse conditions, or even when heated. The stability of such formulations was enhanced in comparison to conventional low pH formulations containing untreated ascorbic acid, e.g., low pH creams containing 10% (w/v) untreated ascorbic acid. It is postulated that the observed stability of the present compositions is afforded by an equilibrium reaction between ascorbic acid and monhydroascorbic acid that maintains a stable solution of ascorbic acid.

The present compositions generally also include a non-toxic zinc salt. The zinc salt may be a water-soluble zinc salt such as zinc sulfate. The zinc salt is generally present in about 0.5 to about 5.0% (w/v). Very effective results can typically be obtained with compositions that include no more than about 3.0% (w/v) zinc salt. For example, a number of present compositions are commonly formulated with about 0.5 to about 2.0% (w/v) zinc sulfate together with the other components described herein.

The composition of the present invention may further include one or more compounds capable of serving as a stimulant of protein synthesis and/or precursor to melanin synthesis. This component is generally present in about 1 to about 10% (w/v), and, for example, between about 3 to about 8% (w/v), based on the total composition. Typically, this component includes a tyrosine compound. As employed herein, a "tyrosine compound" is tyrosine or a compound that is capable of generating tyrosine upon chemical and/or biological transformation. Examples of suitable tyrosine compounds for use in the present compositions include tyrosine, N-acetyltyrosine, tyrosine ethyl ester hydrochloride, and tyrosine phosphate.

The present compositions may also include a compound which can function as an anti-inflammatory agent. Examples of suitable anti-inflammatory agents include anti-inflammatory sulfur-containing compounds and anti-inflammatory aminosugars. The sulfur-containing anti-inflammatory compound is typically a sulfur containing amino acid or related derivative such as cystine, cysteine, N-acetyl cysteine, glutathione, cysteamine, S-methylcysteine, methionine and the like. Examples of suitable anti-inflammatory aminosugars include glucosamine, mannosamine, N-acetylmannosamine, galactosamine, glucosamine-6-phosphate, N acetylglucosamine, N-acetylmannosamine, N-acetylgalactosamine and the like. For example, by adding D-glucosamine hydrochloride to the present compositions (in circa 5-20% (w/v)), cellular damage due to excess sun exposure can be minimized even if applied roughly 12 hours after exposure due to the anti-inflammatory effects of glucosamine in concert with ascorbic acid.

In addition to treating aged or damaged skin, the present invention further includes compositions and methods for treating inflammatory skin ailments such as rosacea, adult acne and like inflammations. Conventional treatment for rosacea includes cortisone therapy that involves continual use of cortisone, which causes connective tissue thinning. Conventional treatment for non-inflammatory rosacea (for example, red face due to surface blood vessels that become even more prominent after exposure to the sun or to the cold) includes metronizole, which is postulated to be an anti-inflammatory agent. Metronizole therapy requires continual use of metronizole while treatment is desired or necessary. Subjects that use cortisone or metronizole, which both require continual use, typically suffer rebound or recurrence of their inflammation after discontinuing use of either agent. The present invention provides a treatment for inflammatory rosacea that does not have the undesirable effects of cortisone and that is effective for individuals that are resistant to cortisone treatment. The present invention provides the further benefit of decreasing or eliminating rebound of rosacea after discontinuance of use.

A composition of the present invention comprising, for example, approximately 14% ascorbic acid, 3.5% tyrosine, 1.5% zinc sulfate and 20% glucosamine in a topical cream, ointment or lotion is effective for the treatment of rosacea that is resistant to prior art treatments. An embodiment of the present invention for the treatment of inflammatory skin ailments such as rosacea includes a composition comprising ascorbic acid in the range of approximately 5% to 20% w/w in a pH range of approximately 3.7 to 4.1 and glucosamine in the range of approximately 10% to 25%. Additional embodiments may further comprise zinc sulfate and/or tyrosine.

A feature of the present invention is the combination of ascorbic acid and glucosamine. These two substances do not ordinarily combine well because the respective pHs are incompatible with each other. Mixing ascorbic acid with glucosamine produces a soured, brown mush unless at least a portion of the ascorbic acid is pretreated. For the combination of the present invention to mix stably, the use of pretreated ascorbic acid, as described above, adjusted to a pH in the range of approximately 3.8 to 4.0, produces a stable mixture of ascorbic acid and glucosamine. As described above, the pretreated ascorbic acid may be present in the range of approximately 10% to 50% of the total ascorbic acid in the formulation.

An embodiment of the present invention was used to treat a 49-year-old woman of Greek descent who had severe rosacea on her face for ten years and had used hydrocortisone constantly during this period to partially control the inflammation. Topical use of the present invention by the subject on the area of inflammation for a week resulted in complete remission of the rosacea.

A second subject was a 34-year-old woman who suffered from disfiguring rosacea on her face for 14 years. The second subject used hydrocortisone to partially control the inflammation, but even so she rarely went out in public and then only with heavy make-up. After failure of the cortisone treatment to provide adequate relief, the subject used an ascorbic acid, zinc sulfate and tyrosine formulation once a day. The ascorbic acid composition provided slight relief, but the subject's rosacea never cleared up adequately. The subject then used the same ascorbic acid formulation to which 20% (w/v) glucosamine had been added. After one week of using an ascorbic acid/glucosamine composition of the present invention, her complexion showed marked improvement. After three weeks of use, substantially all her blemishes disappeared and she no longer has to wear make-up.

A subject used an embodiment of the present invention containing glucosamine for one week. Before using the embodiment, the subject suffered from disfiguring rosacea blemishes on her face. After one week of use, the subject shows marked improvement. In one week, the size of blemishes has decreased and the intensity of the rosacea has abated, although some scarring (resulting from years of severe inflammatory lesions that had not responded to previous treatments) remains.

The ascorbic acid and tyrosine compound components of the present compositions may be formulated in part or whole in a neutralized or salt form. Acceptable amine salts include the acid addition salts (e.g., formed with a free amino group of a tyrosine compound) and may be formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, histidine, procaine and the like. As noted elsewhere herein, since the present compositions have a pH of about 3.5 or above (and typically at least about 3.7) the ascorbic acid is typically at least partially present in the form of ascorbate salt(s), or possibly as an equilibrium reaction between ascorbic acid and monohydroascorbic acid. Commonly, the pH of the composition is adjusted to the desired value by adding sufficient base, such as sodium hydroxide, potassium hydroxide and/or ammonium hydroxide, to achieve the desired value. In such situations, the ascorbate would exist at least in part in the form of sodium hydroxide, potassium and/or ammonium ascorbate.

The water used for preparing the compositions of the present invention may be distilled and/or deionized, but any water may be used that does not contain contaminants that would affect the stability of the ascorbic acid present in the composition. For example, the presence of certain metal ions such as copper and iron salts, is known to affect the stability of ascorbic acid. The effects of water of varying purity on ascorbic acid stability is discussed in Meucci, et al., "Ascorbic Acid Stability in Aqueous Solutions," Acta Vitaminol. Enzymol. 7(34): 147-54 (1985), the disclosure of which is incorporated herein by reference.

The present compositions typically also include a pharmaceutically acceptable carrier. Carriers for topical application useful in practicing the invention include, but are not limited to, alkyleneglycols, or alkyleneglycols in combination with one or more derivatives of hydroxyalkylcellulose. In one illustrative embodiment, the alkylene glycol is propyleneglycol and the hydroxyalkylcellulose is hydroxypropylcellulose. When a combination of alkyleneglycol and hydroxyalkylcellulose is used, a useful ratio of alkyleneglycol to hydroxyalkylcellulose is from about 30:1 to 5:1.

Without limitation, other carriers known to those skilled in the art that are compatible with water and are biologically or pharmaceutically acceptable are expected to provide equivalent compositions within the scope of this invention. For example, alcohols such as ethanol and propanol, glycols such as butylene or hexylene glycol, and polyols such as sorbitol or glycerol may be suitably employed. Other examples of suitable carriers include polyethylene or polypropylene glycols. Also contemplated as carriers for use in the present compositions are biologically acceptable hydroxyalkylcelluloses.

The phrase "pharmaceutically acceptable" refers to molecular entities and compositions that do not produce an allergic or similar untoward reaction when administered to a human. The pharmaceutically acceptable carriers and additives employed in the present compositions are compatible with at least one formulation of the ascorbic acid/ascorbate mixture, tyrosine compound and zinc salt-containing compositions as described herein.

Amino acids employed in the present compositions will generally be in the left-handed chiral form of the amino acid (i.e., L-amino acid(s)). The amino acids should be as pyrogen free as possible and should meet sterility, pyrogenicity, general safety and purity standards as required by FDA Office of Drug standards. The amino acids may even act as buffers for the present solutions or may even be used to adjust the pH of the solution to above 3.5.

Illustrative examples of the present compositions can be produced as follows. The appropriate amounts of the acid forms of native and untreated ascorbic acid are mixed and/or dissolved in water. A water soluble, non-toxic zinc salt is then added and the mixture is mixed (via stirring or agitation) until the zinc salt has dissolved. Other components, such a tyrosine compound and/or anti-inflammatory compounds are then added if desired.

After the other ingredients have been added to the solution, the pH is adjusted by adding an appropriate amount of a base such as sodium hydroxide or sodium carbonate to produce a pH of about 3.8 to about 4.0. The resulting solution can be employed as a topical composition in this form (i.e., a "serum") or may be used to produce any of a variety of conventional formulations well known to those skilled in the art, e.g., as a cream, lotion or gel.

The present topical composition may be in the form of an aqueous solution (i.e., "serum") or blended into a tissue compatible vehicle, such as hydrophilic lotion-, ointment-, cream- or gel-based vehicle. Such vehicles are well known in the art and commercially available for formulation of active ingredients into a suitable form for topical application. Exemplary of such vehicles are the commercially available Dermabase and Unibase formulations.

The present compositions may include one or more of a variety of optional ingredients, such as coloring agents, opacifying agents and the like. The compositions may include, in addition to the components described hereinabove, other active ingredients, such as antibiotics, analgesics, anti-allergenics and the like. The formulation is commonly applied to the skin as a lotion or cream to be rubbed on body tissue over the desired area. For optimum efficacy treatment in accordance with the presented method should be initiated as early as possible following exposure to sunlight or another radiation source or upon the occurrence of a rosacea outbreak, rash, dermatitis, adult acne or other inflammatory skin response. Generally, a composition of the present invention may be applied to the skin once or twice daily. As noted elsewhere herein, the present composition may be used to inhibit the effects of aging and/or photo damage on the skin, or to treat rosacea, rash, dermatitis or other inflammatory skin complaint.

Upon formulation, compositions will be administered in a manner compatible with the formulated dosage and in such amount and frequency as is therapeutically effective. The compositions of the present invention are easily administered in a variety of administration forms suitable for direct topical application on skin. Pharmaceutically acceptable forms of administration include, but are not limited to, lotions, ointments, foams, emollients, microsphere and other encapsulants including time-release encapsulants, patches including, e.g., transdermal patches, shampoos, skin or hair conditioners, pomades, sprays or aerosols, water-based solutions, oil/water emulsifications, gels, sera, unguents, salves, soaps, waxes, paraffins, gums, creams, tonics, elixirs, embrocations, lenitives, liniments, medicaments, balms, balsams, palliatives and any combination of administration forms suitable for topical application on skin.

For topical-administration in an aqueous solution, for example, the ascorbic acid/ascorbate mixture, tyrosine compound and zinc salt containing compositions of the present invention, including those embodiments containing glucosamine or other anti-inflammatory aminosugar, may be used directly on the skin without any toxic effects to the animal or patient. Alternatively, the ascorbic acid/ascorbate mixture, tyrosine compound and zinc salt containing compositions identified herein, including those containing glucosamine or other anti-inflammatory aminosugar, may be dissolved or resuspended in a suitable buffer prior to mixing, if necessary. Liquid diluents may first be rendered isotonic with sufficient saline or glucose solutions.

The present aqueous solutions are especially suitable for topical administration. As discussed above, however, other ascorbic acid-based formulations, including those containing glucosamine or other anti-inflammatory aminosugar, may also be used quite effectively. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The topical compositions of the present invention may be included in lotions and creams, which may be a dermatologically acceptable emollient. Such compositions may contain from about 2% to about 50% of the emollient. An "emollient" as defined herein is a material useful for the prevention or relief of dryness, as well as for the protection of the skin. Many suitable emollients are known and may be used with the present invention, see e.g., Sagarin, Cosmetics, Science and Technology, 2nd Edition, Vol. 1, pp. 32-43 (1972), relevant portions incorporated herein by reference. A material suitable as an emollient is, e.g., glycerin. Glycerin may be used in an amount of from or about 0.001 to or about 20%, from or about 0.01 to or about 10, or even from about 0.1 to or about 5%, e.g., 3%.

Lotions and creams may also include a solution carrier system and one or more emollients. Lotions typically include from about 1% to about 20%, from about 5% to about 10%, of emollient; from about 50% to about 90%, from about 60% to about 80%, water; and other ingredients in the above described amounts. A cream includes typically from about 5% to about 50%, from about 10% to about 20%, of emollient; from about 45% to about 85%, from about 50% to about 75%, water; and other ingredients in the above described amounts.

Ointments of the present invention may include a simple carrier base of animal or vegetable oils or semi-solid hydrocarbons (oleaginous); absorption ointment bases which absorb water to form emulsions; or water soluble carriers, e.g., a water soluble solution carrier. Ointments may further include a thickening agent, such as described in Sagarin, Cosmetics, Science and Technology, 2nd Edition, Vol. 1, pp. 72-73 (1972), incorporated herein by reference, and/or an emollient. For example, an ointment may include from about 2% to about 10% of an emollient; from about 0.1% to about 2% of a thickening agent; and other ingredients in the above described amounts.

Compositions of this invention useful for cleansing ("cleansers") may be formulated with a suitable carrier, e.g., as described above, and contain, in addition to the ingredients in the amounts described above, from about 1% to about 90%, or from about 5% to about 10%, of a dermatologically acceptable surfactant. Surfactants may be selected from anionic, nonionic, zwitterionic, amphoteric and ampholytic surfactants, as well as mixtures of these surfactants. Such surfactants are well known to those skilled in the detergency art. Examples of surfactants include isoceteth-20, sodium methyl cocoyl taurate, sodium methyl oleoyl taurate, and sodium lauryl sulfate, see e.g., U.S. Pat. No. 4,800,197, to Kowcz et al., issued Jan. 24, 1989, relevant portions incorporated herein by reference, for exemplary surfactants. Examples of a broad variety of additional surfactants are described in McCutcheon's Detergents and Emulsifiers, North American Edition (1986), published by Allured Publishing Corporation, relevant portions incorporated herein by reference. The cleansing compositions may contain, at their art-established levels, other materials that are used conventionally in cleansing compositions.

The physical form of the cleansing, cream, lotion and other compositions is not critical. The compositions may be, for example, formulated as toilet bars, liquids, shampoos, bath gels, hair conditioners, hair tonics, pastes, or mousses. Toilet bars may be provided as a cleansing agent most commonly used to wash the skin, e.g., the face or scalp Cleansing compositions that rinse-off, such as shampoos, may require a delivery system adequate to deposit sufficient levels of actives on the skin and scalp. One such delivery system involves the use of insoluble complexes. For a more complete disclosure of such delivery systems, see U.S. Pat. No. 4,835,148, Barford et al., issued May 30, 1989, relevant portions incorporated herein by reference.

The present invention may also be formulation as a foundation. As used herein, the term "foundation" refers to a liquid, semi-liquid, semi-solid, or solid skin cosmetic that includes, but is not limited to lotions, creams, gels, pastes, cakes, and the like. Typically, foundations are used over a large area of the skin, such as over the face, to provide a particular look. Foundations are used typically to provide an adherent base for color cosmetics such as rouge, blusher, powder and the like, and tend to hide skin imperfections and impart a smooth, even appearance to the skin.

Foundations will find particular usefulness in the present invention when used to not only reduce the level of inflammation associated with skin conditions such as rosacea, adult acne and the like, but also provide a make-up that will cover the treatment areas until the skin returns to its pre-inflammatory state. Foundations may include a dermatologically acceptable carrier for the formulations of the present invention, e.g., oils, colorants, pigments, emollients, fragrances, waxes, stabilizers and the like.

The compositions of the present invention may further include a non-toxic zinc salt. Zinc salts for use with the present invention may include zinc acetate, zinc acetate hydrates, zinc aluminum oxide complexes, zinc bromate, zinc bromide, zinc carbonates, zinc chlorate hydrates, zinc chloride, zinc diamine dichloride, zinc citrate, zinc chromate, zinc dichromate, zinc diphosphate, zinc hexacyanofluoride ferrate (II), zinc fluoride, zinc fluoride hydrates, zinc formate, zinc formate hydrates, zinc hydroxide, zinc iodate, zinc iodate, zinc iodide, zinc iron oxide complexes, zinc nitrate hydrates, zinc nitride, zinc oxalate hydrates, zinc oxides, zinc perchlorate, zinc permanganate hydrates, zinc peroxide, zinc p-phenolsulfonate hydrates, zinc phosphate, zinc phosphate hydrates, zinc phosphide, zinc propionate, zinc selenate hydrates, zinc selenide, zinc silicates, zinc silicon oxide water complexes, zinc hexafluorosilicate hydrates, zinc stearate, zinc sulfate, zinc sulfate hydrates, zinc sulfide, zinc sulfite, zinc telluride, zinc thiocyanate, zinc (II) salts of N-acetyl L-cysteine, and mixtures thereof. Zinc salts may also include zinc citrate, zinc oxide, zinc chloride, zinc acetate, zinc stearate, zinc sulfate, and mixtures thereof, with Zinc citrate being particularly useful.

The compositions of the present invention may also include one or more humectants or moisturizers. A variety of these materials may be used at amount ranging from about 0.1% to about 20%, from about 0.5% to about 15%, and from about 1% to about 10%. Examples of humectants include materials selected from the group consisting of guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

A particular humectant for use herein is glycerol. Other materials that may be used in conjunction with the present invention include: almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, cericite, silica, silk, sodium bicarbonate, sodium silicoaluminate, soy flour synthetic hectorite, talc, tin oxide, titanium disoide, tricalcium phosphate, walnut shell powder, wheat bran, wheat flour, wheat starch, zirconium silicate, and mixtures thereof. Also useful are mixed polymers (e.g., copolymers terpolymers, etc.), such as polyethylene/polypropylene copolymer, polyethylene/propylene/isobutylene copolymer, polyethylene/styrene copolymer, and the like. Typically, the polymeric and mixed polymeric particles are treated via an oxidation process to destroy impurities and the like. The polymeric and mixed polymeric particles may also be crosslinked with a variety of common crosslinking agents. Examples of common cross-linking agents include: butadiene, di-vinyl benzene, methylenebisacrylamide, allyl ethers of sucrose, allyl ethers of pentaerythritol, and mixtures thereof. Other examples of useful particles include waxes and resins, such as: paraffins, carnuba wax, ozekerite wax, candellila wax, urea-formaldehyde resins and the like. When waxes and resins are used it is important that these materials are solids at ambient and skin temperatures.

The present invention also includes methods for delivering an effective amount of the composition of the present invention when applied to the skin. These compositions are useful for conditioning and treating e.g., inflamed, dry, aging and damaged skin.

The compositions of the present invention are useful for personal treatment and cleansing, especially of exposed areas of the skin such as face and neck. Typically, a suitable or effective amount of the composition is applied to the area to be treated. Alternatively, a suitable amount of the composition may be applied via intermediate application to a washcloth, sponge, pad, cotton ball or other application device. If necessary, the area to be treated may be cleaned or pre-moistened with water and/or a thin layer of an ointment, cream, oil and the like. It has been found that the compositions of the present invention may cause a mild irritation in patients with sensitive skins when applied directly. In those cases where skin irritation is a problem, the subject may apply a cream or other lotion to the area before using the composition of the present invention to reduce the level of skin irritation. Alternatively, the composition may be used or provided along with and wiped-off from the skin using a pad, cotton ball, tissue or other like device. The cleansing process is typically a two-step process involving application of the composition followed either by rinsing of the produce with water or wiping without the use of water. An effective amount of composition to be used will depend upon the needs of the individual.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description.

What is claimed is:

1. A method of treating rosacea or acne, the method comprising topically applying to the skin of a human afflicted with rosacea or acne an effective amount of a composition comprising:
    at least 10% (w/v) ascorbic acid;
    approximately 10% to 25% (w/v) glucosamine; and
    water,
    wherein the composition has a pH of about 3.5 to about 4.1; and
    wherein the composition is prepared by a process comprising:
    (a) dissolving about 10% to about 50% of the ascorbic acid in water at a temperature of between about 60° C. to about 90° C. to provide an aqueous ascorbic acid solution of at least 20% (w/v);
    (b) cooling the aqueous ascorbic acid solution to below about 40° C.;
    (c) combining the aqueous ascorbic acid solution with water, glucosamine, and ascorbic acid to provide a composition comprising water, approximately 10% to 25% (w/v) glucosamine and at least 10% (w/v) ascorbic acid; and
    (d) adjusting the pH of the composition to about 3.5 to about 4.1.

2. The method of claim 1, wherein the ascorbic acid is present in an amount of about 15% to about 25% (w/v) of the composition.

3. The method of claim 1, wherein the ascorbic acid is present in an amount of about 15% (w/v) of the composition.

4. The method of claim 1, wherein the water is distilled or deionized water.

* * * * *